United States Patent
Madden

(10) Patent No.: US 7,276,060 B2
(45) Date of Patent: Oct. 2, 2007

(54) SURGICAL HANDPIECE TIP

(75) Inventor: Sean C. Madden, Mission Viejo, CA (US)

(73) Assignee: Alcon, Inc., Hunenberg (CH)

( * ) Notice: Subject to any disclaimer, the term of this patent is extended or adjusted under 35 U.S.C. 154(b) by 482 days.

(21) Appl. No.: 10/787,630

(22) Filed: Feb. 26, 2004

(65) Prior Publication Data

US 2005/0192566 A1 Sep. 1, 2005

(51) Int. Cl.
*A61B 18/18* (2006.01)
*A61B 18/04* (2006.01)

(52) U.S. Cl. .......................... 606/27; 606/39

(58) Field of Classification Search ................. 606/27, 606/39, 171, 41, 45, 48
See application file for complete search history.

(56) References Cited

U.S. PATENT DOCUMENTS

| | | |
|---|---|---|
| 3,589,363 A | 6/1971 | Banko et al. |
| 3,606,878 A | 9/1971 | Kellog |
| 3,818,913 A | 6/1974 | Wallach |
| 3,884,237 A | 5/1975 | O'Malley et al. |
| 3,913,583 A | 10/1975 | Bross |
| 3,930,505 A | 1/1976 | Wallach |
| 3,994,297 A | 11/1976 | Kopf |
| 4,024,866 A | 5/1977 | Wallach |
| 4,169,984 A | 10/1979 | Parisi |
| 4,223,676 A | 9/1980 | Wuchinich |
| 4,246,902 A | 1/1981 | Martinez |
| 4,301,802 A | 11/1981 | Poler |
| 4,326,529 A | 4/1982 | Doss et al. |
| 4,493,694 A | 1/1985 | Wuchinich |
| 4,494,539 A | 1/1985 | Zenitani et al. |
| 4,517,977 A | 5/1985 | Frost |

(Continued)

FOREIGN PATENT DOCUMENTS

EP 0 536 440 5/1997

(Continued)

OTHER PUBLICATIONS

Cowley, Geoffrey, "Beating the Back Ache", Newsweek, Mar. 15, 1999.

(Continued)

*Primary Examiner*—Roy D. Gibson
*Assistant Examiner*—Pete Vrettakos
(74) *Attorney, Agent, or Firm*—Jeffrey S. Schira

(57) ABSTRACT

A surgical handpiece having a tip with at least two coaxially spaced electrically conductive tubes. The tubes are separated by an electrical insulator. The interior of the inner tube is used for aspiration of liquefied tissue. The outer tube is surrounded by a soft irrigation sleeve that forms an irrigation fluid path. The distal portion of the interior tube terminates inside of the outer tube so as to form a boiling region. Surgical fluid from the irrigation fluid path can enter the boiling region through a hole or port in the outer tube. Electrical current is passed between the inner and outer tube to rapidly boil any surgical fluid in the boiling region. The boiling fluid rapidly expands out of the ring between the tube ends and forces hot fluid to contact the targeted tissue, thereby liquefying the tissue and allowing the tissue to be aspirated. Such a construction allows the boiling chamber to be self-priming and operate even if the outer tube is occluded with material.

7 Claims, 3 Drawing Sheets

U.S. PATENT DOCUMENTS

| | | |
|---|---|---|
| 4,534,347 A | 8/1985 | Taylor |
| 4,570,632 A | 2/1986 | Woods |
| 4,577,629 A | 3/1986 | Martinez |
| 4,589,414 A | 5/1986 | Yoshida et al. |
| 4,589,415 A | 5/1986 | Haaga |
| 4,597,388 A | 7/1986 | Koziol et al. |
| 4,609,368 A | 9/1986 | Dotoson, Jr. |
| 4,634,419 A | 1/1987 | Kreizman et al. |
| 4,634,420 A | 1/1987 | Spinosa et al. |
| 4,662,869 A | 5/1987 | Wright |
| 4,674,499 A | 6/1987 | Pao |
| 4,674,502 A | 6/1987 | Imonti |
| 4,682,596 A | 7/1987 | Bales |
| 4,696,298 A | 9/1987 | Higgins et al. |
| 4,706,669 A | 11/1987 | Schlegel |
| 4,753,234 A | 6/1988 | Martinez |
| 4,805,616 A | 2/1989 | Pao |
| 4,909,249 A | 3/1990 | Akkas et al. |
| 4,911,161 A | 3/1990 | Schechter |
| 4,922,902 A | 5/1990 | Wuchinich et al. |
| 4,986,827 A | 1/1991 | Akkas et al. |
| 4,989,583 A | 2/1991 | Hood |
| 4,989,588 A | 2/1991 | Kubota et al. |
| 5,009,656 A | 4/1991 | Reimels |
| 5,019,035 A | 5/1991 | Missirlian et al. |
| 5,106,364 A | 4/1992 | Hayafuji et al. |
| 5,154,694 A | 10/1992 | Kelman |
| 5,201,729 A | 4/1993 | Hertzmann et al. |
| 5,217,459 A | 6/1993 | Kamerling |
| 5,226,910 A | 7/1993 | Kajiyama et al. |
| 5,433,739 A | 7/1995 | Sluijter |
| 5,616,120 A | 4/1997 | Andrew et al. |
| 5,885,243 A | 3/1999 | Capetan |
| 6,156,036 A | 12/2000 | Sussman et al. |
| 6,183,469 B1 * | 2/2001 | Thapliyal et al. .............. 606/41 |
| 6,398,759 B1 * | 6/2002 | Sussman et al. ............ 604/114 |
| 6,629,986 B1 * | 10/2003 | Ross et al. ................... 606/171 |

FOREIGN PATENT DOCUMENTS

| | | |
|---|---|---|
| WO | WO 97/00646 | 1/1997 |
| WO | WO 97/18766 | 5/1997 |
| WO | WO 98/17190 | 4/1998 |

OTHER PUBLICATIONS

Fletcher, et al, "Pulsed Liquid microjet for microsurgery", Applied Physics Letters, vol. 78, No. 13, Mar. 26, 2001.

* cited by examiner

SURGICAL HANDPIECE TIP

BACKGROUND OF THE INVENTION

This invention relates generally to the field of minimally invasive surgery, such as intervertebral disc and cataract surgery and more particularly to a handpiece for practicing the liquefraction technique.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

Recently, a new tissue removal technique has been developed that involves the injection of hot (approximately 45° C. to 105° C.) water or saline to liquefy or gellate tissue, such as the hard lens nucleus, thereby making it possible to aspirate the liquefied tissue. Aspiration is conducted with the injection of the heated solution and the injection of a relatively cool solution, thereby quickly cooling and removing the heated solution. One application of this technique is more fully described in U.S. Pat. No. 5,616,120 (Andrew, et al.), the entire contents of which is incorporated herein by reference. The apparatus disclosed in the publication, however, heats the solution separately from the surgical handpiece. Temperature control of the heated solution can be difficult because the fluid tubings feeding the handpiece typically are up to two meters long, and the heated solution can cool considerably as it travels down the length of the tubing.

The use of electrosurgical handpieces to remove tissue is known. For example, U.S. Pat. No. 5,009,656 (Reimels), the entire contents of which is incorporated herein by reference, describes an electrosurgical handpiece having an inner and an outer tube separated by an insulator. Current is passed between the inner and the outer tube to cause a spark that is used to cut tissue. This device intentionally creates an air gap between the electrodes to facilitate sparking, and does not use heated fluid as the cutting medium.

In addition, U.S. Pat. No. 6,156,036 (Sussman, et al.), the entire contents of which, and particularly the material at column 2, lines 40-67, column 3, lines 1-67 and column 4, lines 1-27, being incorporated herein by reference, discloses a surgical handpiece having a tip with at least two coaxially spaced electrically conductive tubes. The tubes are separated by an electrical insulator. The interior of the inner tube is used for aspiration of liquefied tissue. The distal portion of the interior tube terminates just inside of the outer tube so as to form a boiling region. Electrical current is passed between the inner and outer tube to rapidly boil any surgical fluid in the boiling region. The boiling fluid rapidly expands out of the ring between the tube ends and forces hot fluid to contact the targeted tissue, thereby liquefying the tissue and allowing the tissue to be aspirated. This reference, however, does not describe a tip having a source of irrigation fluid. Fluid must enter the boiling region through the aspiration opening. The aspiration opening is occluding by the material being ablated, the boiling chamber may not fill with surgical fluid.

Therefore, a need continues to exist for a surgical handpiece that can heat internally the solution and create high pressure, high rise rate waves or pulses used to perform the liquefraction technique and that contains a pathway for surgical fluid to enter the boiling chamber even if the aspiration opening is occluded.

BRIEF SUMMARY OF THE INVENTION

The present invention improves upon the prior art by providing a surgical handpiece having a tip with at least two coaxially spaced electrically conductive tubes. The tubes are separated by an electrical insulator. The interior of the inner tube is used for aspiration of liquefied tissue. The outer tube is surrounded by a soft irrigation sleeve that forms an irrigation fluid path. The distal portion of the interior tube terminates inside of the outer tube so as to form a boiling region. Surgical fluid from the irrigation fluid path can enter the boiling region through a hole or port in the outer tube. Electrical current is passed between the inner and outer tube to rapidly boil any surgical fluid in the boiling region. The boiling fluid rapidly expands out of the ring between the tube ends and forces hot fluid to contact the targeted tissue, thereby liquefying the tissue and allowing the tissue to be aspirated. Such a construction allows the boiling chamber to be self-priming and operate even if the outer tube is occluded with material.

Accordingly, one objective of the present invention is to provide a surgical handpiece having a tip with at least two tubes.

Another objective of the present invention is to provide a handpiece for practicing the liquefraction method of tissue removal.

Another objective of the present invention is to provide a self-priming surgical handpiece having a tip with at least two coaxial tubes.

These and other advantages and objectives of the present invention will become apparent from the detailed description and claims that follow.

DETAILED DESCRIPTION OF THE INVENTION

Figure 1:
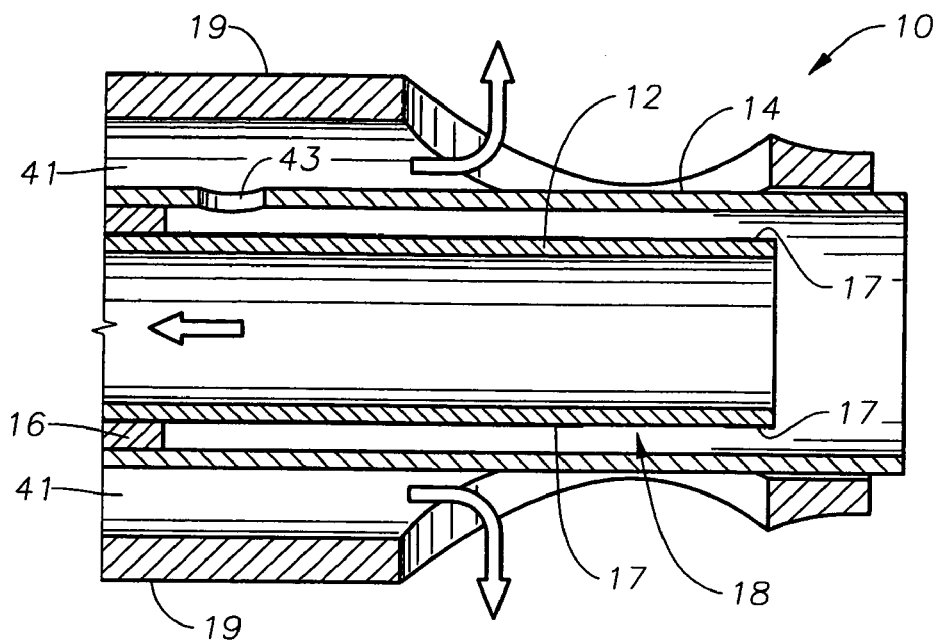
FIG. 1 is a schematic, cross-sectional view of a tip that can be used with the handpiece of the present invention, the tip being in an unoccluded state.
Figure 3:
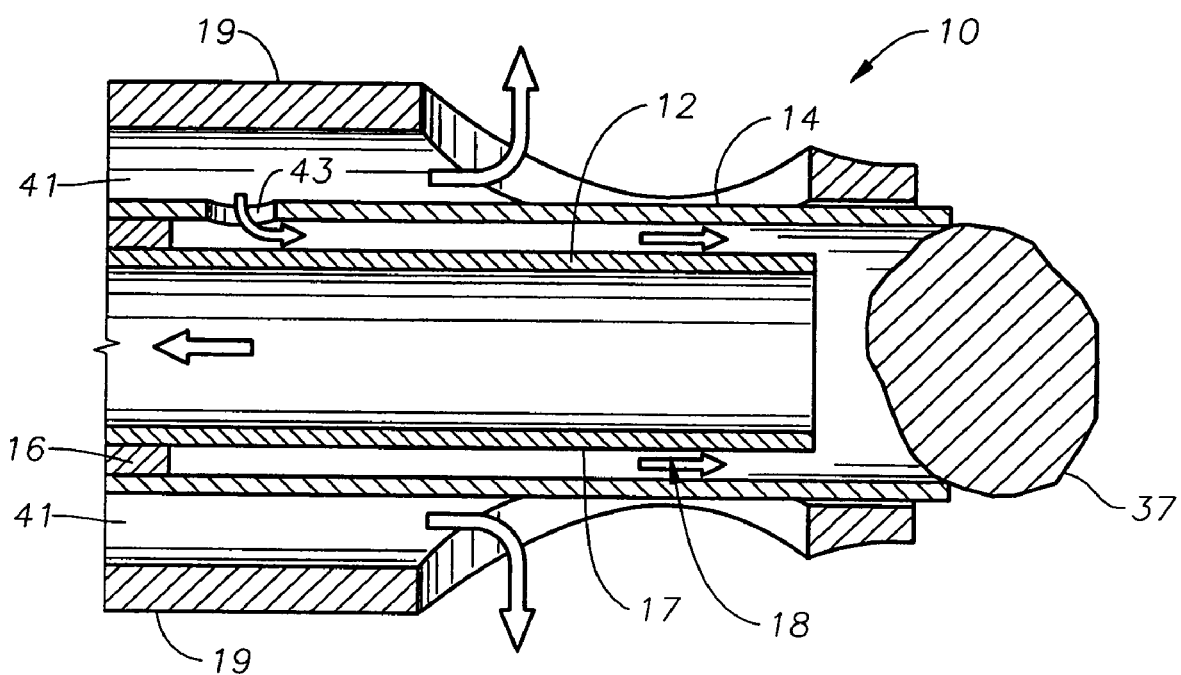
FIG. 3 is a schematic, cross-sectional view similar to FIG. 1 of a tip that can be used with the handpiece of the present invention, the tip being in an occluded state.

As best seen in FIGS. 1 and 3, in the present invention tip 10 to be used with handpiece 9 generally includes inner tube 12 and outer tube 14 separated by insulator 16. Inner tube 12 has any suitable inside diameter, such as about 0.028 inches, and any suitable outside diameter, such as about 0.032 inches. Outer tube 14 has any suitable outside diameter, such as about 0.042 inches. Inner tube 12 and outer tube 14 may be made of any electrically conductive material, such as stainless steel or titanium tubing. Insulator 16 may be made of any electrically nonconductive material resistant to high temperatures, such as polyimide, silicone or ceramic. Insulator 16 may be any suitable thickness, for example, about 0.003 inches. Inner tube 12 may also contain dielectric coating 17 having a portion removed so as to form an annular boiling region 18. Coating my be any suitable material, with vapor deposited parylene being preferred.

Outer tube 14 extends distally past inner tube 12 a distance of between 0.00 inches 10 and 0.028 inches, with about 0.014 inches being preferred. Insulator 16 terminates prior to the termination of inner tube 12 so that inner tube 12 extends distally past inner insulator 16. The portion of inner tube 12 extending past insulator 16 contains coating 17. Boiling region 18 is located in the space between outer tube 14 and inner tube 12. While only one embodiment of the tip of the present invention is disclosed herein, any tip producing adequate pressure pulse force, rise time and frequency may also be used. For example, any suitable tip producing a pressure pulse force of between 0.01 grams and 50.0 grams, with a rise time of between 1 gram/sec and 50,000 grams/sec, with between 5000 grams/sec and 50,000 grams/sec being more preferred and a frequency of between 1 Hz and 10 kHz may be used, with between 25 Hz and 250 Hz being most preferred.

In use, surgical fluid (e.g. saline irrigating solution) enters boiling region 18. Electrical current (preferably Radio Frequency Alternating Current "RFAC") is delivered to and across inner tube 12 and outer tube 14 through the surgical fluid in boiling region 18 because of the conductive nature of the surgical fluid. As the current flows through boiling region 18, the surgical fluid boils. As the surgical fluid boils, it expands. As the bubble(s) expand, some of the surgical fluid is pushed out of tip 10 creating a fluid pulse. When the bubble(s) collapse, a vacuum is created. This vacuum pulls in more surgical fluid and refills boiling region 18. Subsequent pulses of electrical current form sequential gas bubbles. The size and pressure of the fluid pulse obtained by boiling region 18 can be varied by varying the length, timing and/or power of the electrical pulse sent to tubes 12 and 14 and by varying the dimensions of boiling region 18.

As best seen in FIG. 3, when tip 10 is occluded by material 37, surgical fluid cannot enter boiling region 18 through outer tip 14. To account for this situation, tip 10 also includes outer irrigation sleeve 19, which is similar in construction to existing silicone irrigation sleeves well-known in the art. Sleeve 19 surrounds outer tube 14 and forms annular irrigation path 41 between sleeve 19 and outer tube 14 for a surgical fluid. Irrigation path 41 is connected to a source of irrigation fluid under positive pressure through irrigation line 322. Outer tube 14 contains bypass port 43 that allows fluid communication between irrigation path 41 and boiling region 18. In the event that outer tube 14 becomes occluded by material 37, bypass port 43 allows surgical fluid to enter boiling region 18 from irrigation path 41. In addition, aspiration vacuum may be used to assist chamber priming.

Figure 2:
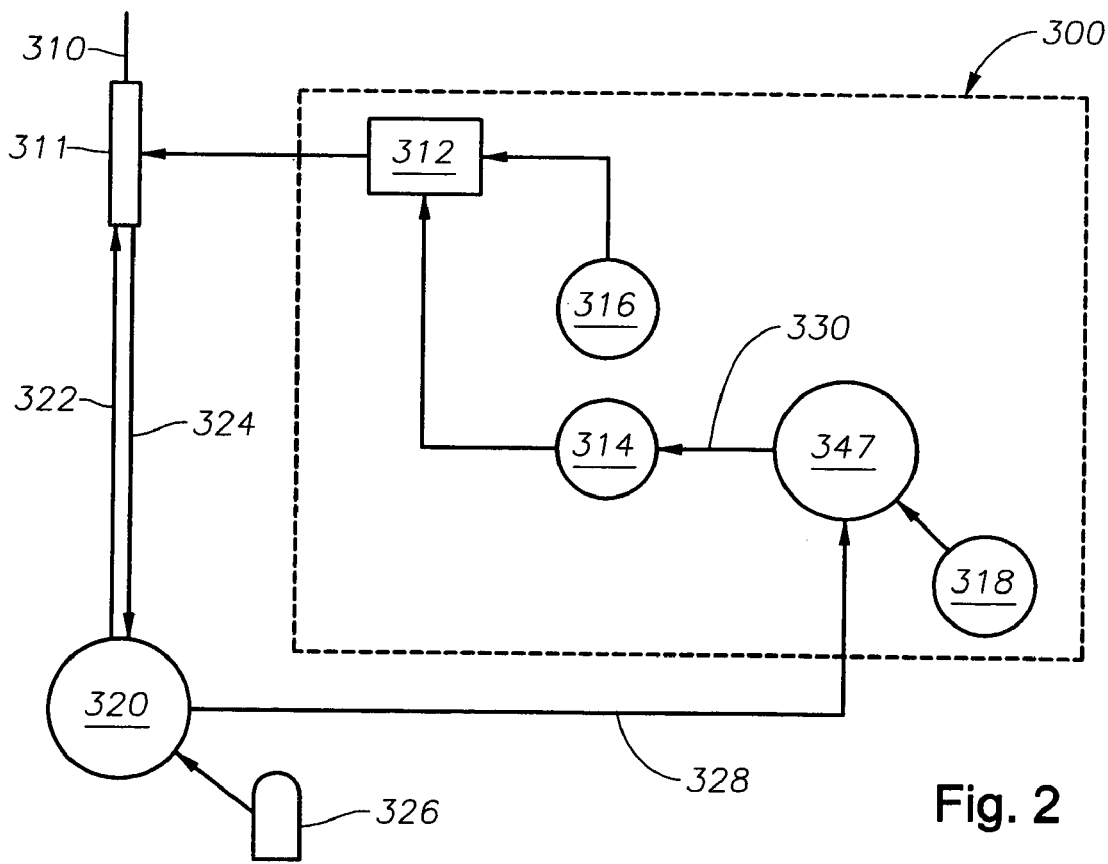
FIG. 2 is a block diagram of a first control system that can be used with the surgical handpiece of the present invention.
Figure 4:
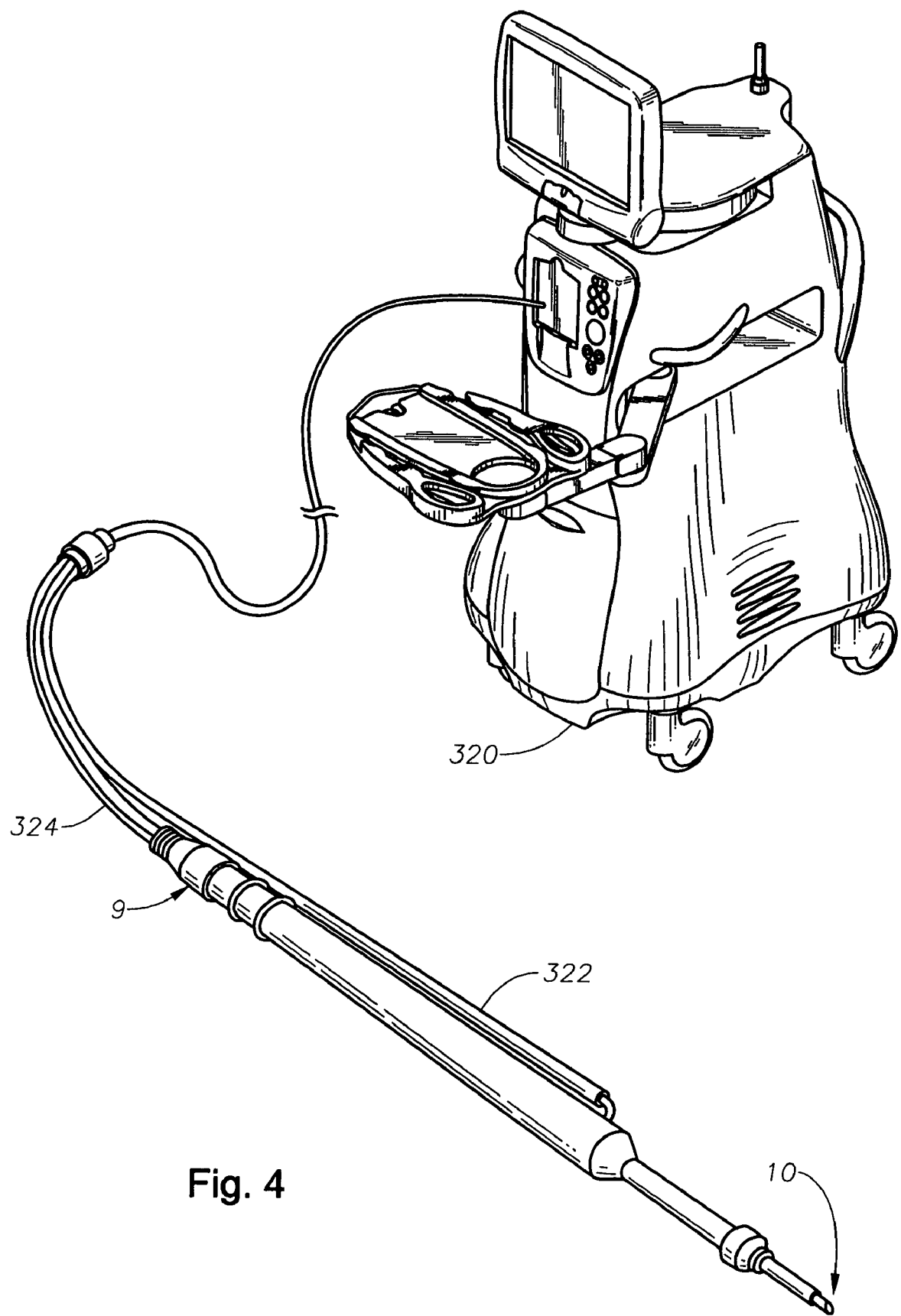
FIG. 4 is a perspective view of a handpiece and control console that may be used with the present invention.

As seen in FIGS. 2 and 4, control system 300 for use in operating handpiece 9 containing tip 10 includes control module 347, RF amplifier 312 and function generator 314. Power is supplied to RF amplifier 312 by DC power supply 316, which preferably is operating at 75 volts. Control module 347 may be any suitable microprocessor, and may receive input from operator input device 318. Function generator 314 provides the electric wave form to amplifier 312 and preferably operates at 200 KHz to 10 MHz, and more preferably above 750 KHz, to help minimize corrosion.

In use, control module 347 receives input from surgical console 320. Console 320 may be any commercially available surgical control console such as the LEGACY® SERIES TWENTY THOUSAND® or INFINITI® surgical systems available from Alcon Laboratories, Inc., Fort Worth, Tex. Console 320 is connected to handpiece 9 through irrigation line 322 and aspiration line 324, and the flow through lines 322 and 324 is controlled by the user, for example, via footswitch 326. Irrigation and aspiration flow rate information in handpiece 9 is provided to control module 347 by console 320 via interface 328, which may be connected to a handpiece control port on console 320 or to any other output port. Control module 347 uses footswitch 326 information provided by console 320 and operator input from input device 318 to generate two control signals 330 and 332. Signal 330 is used to control function generator 314. Based on signal 330, function generator 314 provides a wave form at the operator selected frequency and amplitude determined by the position of footswitch 326 to RF amplifier 312 which is amplified to advance the powered wave form to tip 10 to create heated, pressurized pulses of surgical fluid.

The present invention may also be used for intervertebral disc surgery, such as intradisc thermal annuloplasty. During this surgery, the ligaments encasing a spinal disc are heated to destroy invading veins and nerves and to shrink the ligaments to seal any tears or ruptures.

This description is given for purposes of illustration and explanation. It will be apparent to those skilled in the relevant art that changes and modifications may be made to the invention described above without departing from its scope or spirit. For example, it will be recognized by those skilled in the art that the present invention may be combined with ultrasonic and/or rotating cutting tips to enhance performance.

I claim:

1. A handpiece tip comprising:
   a) an inner electrically conductive aspiration tube having a distal end:
   b) an outer electrically conductive tube having a distal and coaxially spaced about the inner tube, the distal end of the outer tube extending distally past the distal end of the inner tube;
   c) an insulator spaced between the inner tube and the outer tube;
   d) an irrigation sleeve surround the outer tube and forming an irrigation path through which a surgical fluid can flow;
   e) a boiling region formed by the outer between the distal end of the outer tube and the distal end of the inner tube; and
   f) a bypass port fluidly connecting the irrigation path with the boiling region.

2. The tip of claim 1 wherein the electrical current flowing across the electrode is capable of boiling the surgical fluid.

3. The tip of claim 1 wherein the inner tube contains a dielectric coating and the boiling region is formed by removing a portion of the dielectric coating on the inner tube.

4. The tip of claim 1 wherein the electrical current flowing across the electrodes is capable of producing a pressure pulse force of between 0.01 grams and 50.0 grams in a fluid.

5. A handpiece tip comprising:
   a) an inner electrically conductive aspiration tube having a distal end and containing a dielectric coating;

b) an outer electrically conductive tube having a distal end coaxially spaced about the inner tube, the distal end of the outer tube extending distally past the distal end of the inner tube:
c) an insulator spaced between the inner tube and the outer tube;
d) an irrigation sleeve surround the outer tube and forming an irrigation path through which a surgical fluid can flow;
e) a boiling region formed by removing a portion of the coating from the inner tube, the boiling region being located between the distal end of the outer tube and the distal end of the inner tube; and
f) a bypass port fluidly connecting the irrigation path with the boiling region.

6. The tip of claim 5 wherein the electrical current flowing across the electrodes is capable of boiling the surgical fluid.

7. The tip of claim 5 wherein the electrical current flowing across the electrode is capable of producing a pressure pulse force of between 0.01 grams and 50.0 grams in a fluid.

* * * * *